United States Patent [19]
Erlanson-Albertsson

[11] Patent Number: 5,494,894
[45] Date of Patent: Feb. 27, 1996

[54] AGENT FOR THE REGULATION OF THE APPETITE OR A SLEEPING AGENT

[75] Inventor: Charlotte Erlanson-Albertsson, Uardavägen 8F, S-223 71 Lund, Sweden

[73] Assignee: Charlotte Erlanson-Albertsson, Lund, Sweden

[21] Appl. No.: 26,254

[22] Filed: Mar. 4, 1993

Related U.S. Application Data

[63] Continuation of Ser. No. 819,623, Jan. 9, 1992, abandoned, which is a continuation of Ser. No. 122,079, Nov. 18, 1987, abandoned.

[30] Foreign Application Priority Data

Nov. 20, 1986 [SE] Sweden .................................. 8604953
Jun. 1, 1987 [SE] Sweden .................................. 8702274

[51] Int. Cl.$^6$ ........................... A61K 38/00; A61K 31/74
[52] U.S. Cl. ............................. 514/12; 514/17; 514/910; 424/78.01; 424/78.17; 424/78.27
[58] Field of Search ............................. 514/17, 12, 910; 424/78.01, 78.17, 78.27

[56] References Cited

U.S. PATENT DOCUMENTS 4,491,578  1/1985  Peikia ........................................... 514/2
4,948,723  8/1990  Hermon-Taylor .

FOREIGN PATENT DOCUMENTS 0269595  11/1987  European Pat. Off. ................. 514/17
0258995  3/1988  European Pat. Off. .

OTHER PUBLICATIONS

FEBS Letter, vol. 126, No. 1, Apr. 1981, pp. 25–28, B. Borgstron et al.: "Effect on fenfluroamine & related compounds on the pancreatic colipase/lipase system".
Reprod. Nutr. Develop., vol. 23, No. 1, 1983, pp. 137–144, A. Girard-Globa et al.: "pancreatic hydrolases in cold-induced hyperphagia of rats fed a low or high fat diet".
Diabetes & Metabolisme, vol. 10, No. 1, 1984, pp. 52–62 C. Leger: "Données recentes sur la lipase et la colipase pancreatiques".
Biocheme, vol. 70, 1988, pp. 1245–1250, C. Erlanson-Albertson et al: "A possible physiological function of pancreatic pro-colipase activation peptide in appetite regulation".
Svensk Farmaceutisk Tidskrift, vol. 83, No. 12, 1979, p. 476.
Sternby, B., Biochimica Biophysica Acta, 784: 75–80 (1984).
Gangola, P. et al., *JBC,* 261 (19): 8601–3, 1986.
Erlanson-Albertsson, C., et al., *Regulatory Peptides,* 22: 325–331, 1988.
Borgstrom, B., et al., *Lipases,* Borgstroy, B. (Ed.), Brochman, H. (Ed.), Elsevier, pp. 151–183, 1984.
Sternby, et al., *Biochimic et Biophysica Acta,* 786: 109–112, 1984.
Erlanson, C., et al., *Biochimica et Biophysica Acta,* 310: 437–445, 1973.
Erlanson-Albertsson, C., et al., *Biochimie,* 70: 1245–1250, 1988.
Kissileff, et al., Amer. J. of Clinical Nutrition, 34: 154–160, 1981.
Morley, J., *Life Sciences,* 27: 355–368, 1980.
Luhaszewshi, L., Effects of Continuous Infusions of CCK-8, 1988, R17–R22, the American Physiological Society.
Erlanson-Albertsson, Chorlotte, Biochimica et Biophysica Acta, 666, 299–300, 1981.
Wieloch, Tadeusz, FEBS Letters, 185(1), 63–66, Jun., 1985.
Erlanson-Albertsson, Charlotte, FEBS Letters, 138(1), 125–127, Feb. 1982.

*Primary Examiner*—Jill Warden
*Assistant Examiner*—Sheela J. Huff
*Attorney, Agent, or Firm*—White & Case

[57] ABSTRACT

An agent for the regulation of the appetite or a sleeping agent, which consists of the activation peptide in procolipase, consisting of the peptide sequence X-Pro-Y-Pro-Arg wherein
a) X is Ala and Y is Gly, or
b) X is Val and Y is Asp, or a derivative thereof.

4 Claims, No Drawings

AGENT FOR THE REGULATION OF THE APPETITE OR A SLEEPING AGENT

This application is a continuation of application Ser. No. 7/819,623, filed on Jan. 9, 1992, now abandoned, which is a continuation application of U.S. Ser. No. 07/122,079, filed Nov. 18, 1987 (Abandoned).

The present invention is directed to an agent for the regulation of the appetite or a sleeping agent comprising the activation peptide of colipase occurring in procolipase.

Obesity can be associated with serious and life threatening disorders such as diabetes mellitus, arteriosclerosis, hypertension, angina pectoris, thrombosis and pickwickian syndrome. Reduction of obesity by appetite regulation can therefore be useful in the treatment of such disorders.

The pancreas is made up of two parts, an exocrine part and an endocrine part. From the exocrine part are secreted enzymes which take part in the hydrolysis of food and from the endocrine part is secreted a number of hormones, above all insulin which takes part in the regulation of blood sugar.

Our food consists of macromolecules. There are three main groups, proteins, fats and carbohydrates. In order to be able to be assimilated they must be broken down into smaller pieces, amino acids, fatty acids and monosaccharides. This degradation takes place in the intestine by the action of enzymes. Most of these originate from the pancreas. There are one or more for each group of food, one amylase, which splits starch (carbohydrate), five different proteases, which split proteins (trypsin, chymotrypsin, elastase, carboxypeptidase A and B), and three different enzymes, which split fats (lipase, phospholipase and carboxylesterhydrolase). The most important of these is lipase. It hydrolyses triglycerides (neutral fat), which constitutes the main part of the dietary fat. To emulsify the fat in the intestine all higher animals have bile salt, derived from the liver via the gall-bladder. Lipase itself is totally inhibited by bile salt, but is activated in this situation by another pancreatic protein, colipase. Colipase is a protein with a molecular weight of 10 kD. During the activation of lipase colipase binds to lipase in a 1:1 molar ratio. Colipase itself has no enzyme activity of its own. The activation of lipase by colipase occurs both with and without bile salt; the activating effect is most obvious in the presence of bile salt.

The amino acid sequence of colipase is known. It is a molecule which is stable to heat and acid (is unaffected by boiling in 0,1 N HCl) probably due to its content of five disulphide bridges. It can be characterized as consisting of a core strongly connected by the five disulphide bridges+two tails, the N-terminal and the C-terminal chain. The activation of lipase takes place by binding of colipase to lipase and the subsequent binding to the substrate by the lipase-colipase-complex.

All pancreatic enzymes (with the exception of amylase and lipase) are secreted from pancreas in an inactive or zymogen form and are activated in the intestine by a limited proteolysis. The occurrence of inactive enzymes in the pancreatic gland is a necessary protection against an enzymatic degradation of the pancreatic gland itself (autolysis). At the activation an N-terminal peptide is removed, known as an activation peptide. Every enzyme has its own characteristic activation peptide, consisting of between 5 and 10 amino acids. Enteropeptidase in the small intestine triggers the activation by activating trypsinogen to trypsin, whereafter trypsin activates the remaining pancreatic zymogens.

Colipase exists as a proform, procolipase. The activation peptide for this consists of five amino acids. By most animals (pig, rat, horse) it has the appearance Val-Pro-Asp-Pro-Arg. By man it has the appearance Ala-Pro-Gly-Pro-Arg. This peptide appears to possess biological properties, and can, therefore, be used pharmacologically as an agent for the regulation of the appetite and as a sleeping agent.

The present invention thus concerns an agent for the regulation of the appetite and a sleeping agent, characterized in that it is composed of the activation peptide of procolipase, consisting of the peptide sequence X-Pro-Y-Pro-Arg wherein
a) X is Ala and Y is Gly, or
b) X is Val and Y is Asp or a derivative thereof.

A derivative of this sequence can be made up by natural procolipase, by a C-terminal amide or by the peptide sequence bound to a synthetic polymer.

The preparation of the pentapeptide Ala-Pro-Gly-Pro-Arg and Val-Pro-Asp-Pro-Arg can be performed by synthesis on solid phase (Solid phase peptide synthesis, 2nd Edition, Stewart J. M. and Young J. D. Pierce Chemical Company (1984)).

In order to be able to be administered orally the agent could be derivatized, that is bound to a longer molecule, thus preventing it from being destroyed in the acid environment of the stomac already. The activation peptide shall not be liberated until it has reached the intestine.

Systematic experiments on rats have demonstrated that they lose their appetite and weight when given injections of the pentapeptide. The rats given the pentapeptide also show besides satiety drowsiness, muscle relaxation and sleep. The agent according to the invention can, therefore, be used as a regulator of the appetite as well as a sleeping agent with the great advantage that the agent is naturally occurring.

Overweight in persons can in some instances be due to an enhanced appetite. It has been shown that when persons of normal weight eat with a certain rate of speed in the beginning of the meal and then slower, overweight persons eat with undecreased rate of speed throughout the whole meal. It takes long before satiety is reached.

If the experiments on rat are translated to the social being man the hypothesis is that the overweight person has low or lower levels of procolipase in the pancreas gland and, therefore, a lower amount of peptide in its serum. Overweight persons correspond to the controls in the rat experiments, which eat a lot without pause before they are satisfied. Three hours later, however, they watch the time and observe that it is time to eat again (the social pattern) and sit down to dinner without actually being hungry. The pattern of food intake becomes a habit. The consequence is overweight. Persons of normal weight correspond in the present experiment to the peptide rat, which eats and becomes satisfied comparatively promptly. Three hours later, when it is time for the next meal, these persons are, therefore, hungry. Appetite and pattern of food intake corresponds well by these persons and normal weight is a consequence. These persons have hypothetically more procolipase in their pancreas gland and therefore more activation peptide in their blood than the overweight persons.

It is described (Kissileif et al., Am. J. Clin. Nutr. 34:154–160) that cholocystokinin (CCK) administered intravenously can give to patients an earlier feeling of satiety. CKK is a hormone which stimulates the secretion of pancreatic enzymes and among these procolipase. The previous studied effect may be an indirect effect of CCK, with the peptide according to the invention as a mediator of the effect. This should strengthen the hypothesis that the experiments on rats described here can be translated to man and have use within human medicine.

Instead of administering the peptide intraperitoneally it can be given by the intravenous route. It is also relevant to give it in the form of procolipase included in pellets. A rat given procolipase enriched pellets shows a peptide pattern in its food intake. In this case procolipase obviously passes the stomac in intact form and is activated in the intestine by the trypsin of the rat itself, thus liberating the pentapeptide. This observation is important in relation to possible compositions of the pentapeptide in tablet form (as a stable procolipase molecule). In experiments larger doses have resulted in a reduction of the weight or rather a diminishing increase of the weight in growing rats.

The peptide according to the invention can be used as a drug, for instance in the form of pharmaceutical compositions. The pharmaceutical compositions can be administered orally, for instance in the form of tablets, film coated tablets, dragées, hard and soft gelatine capsules, solutions, emulsions or suspensions. The peptide can also be enclosed in microcapsules. The administration can also be rectally, for instance in the form of suppositories or parenterally, for instance in the form of solutions for injection. The peptide can also be administered as a nose spray or powder. Finally the administration as sublinguett should be mentioned.

For the preparation of tablets, film coated tablets, dragées and hard gelatine capsules the peptide can be mixed with pharmaceutically inert, inorganic or organic excipients. For tablets, dragées and hard gelatine capsules such excipients can be lactose, corn starch or derivatives thereof, talc, stearin acid or salts thereof, etc.

For soft gelatine capsules vegetable oil, wax, fats, semisolid and liquid polyols etc, are suitable as excipients.

For the preparation of solutions and sirups water, polyol, saccharose, invert sugar, glucose and the like are suitable as excipients.

For solutions for injection water, alcohol, polyol, glycerine, vegetable oil etc are suitable as excipients.

For suppositories natural or hardened oil, wax, fat, semiliquid or liquid polyol and the like are suitable as excipients.

The pharmaceutical compositions can also contain preservatives, stabilizers, emulgators, sweeteners, colouring matters, flavourings, salts for changing the osmotic pressure, buffers, sugar coatings or antioxidants. They can also contain further therapeutically valuable agents.

The dosage of the pentapeptide according to the invention to homo should lie within the interval 1–100 mg/day, preferably 1-20 mg/day. The pentapeptide should be given at each meal.

The invention is illustrated by the following non-limiting examples.

EXAMPLE

Regulation of the appetite

Systematic experiments on rats have demonstrated that they lose their appetite and weight when given injections of the pentapeptide. The experiments were designed in such a manner that the rats had to accustom themselves to a four hour period in order to meet their daily nourishment. This consisted of standard pellets. 15 minutes before the food was presented the rats were given an intraperitoneal injection containing peptide or saline, respectively, and food intake was measured at times 0, 30 minutes, 60 minutes, 2 hours and 4 hours. The rats were given saline one day, peptide the following day, saline etc. A typical peptide pattern and a saline pattern (TABLE I) could be observed. The control rat ate a lot in the beginning and had consumed its whole daily need after two hours. The peptide rat on the contrary had satisfied its hunger earlier, stopped eating after about 1 hour and had then eaten 60–80 percent of its daily need (depending on the dosage of the peptide), rested and slept for an hour, grew hungry again and consumed the rest of its daily need between 2–4 hours.

In these short term experiments the amount of consumed food was the same with and without peptide (10–15 g), the peptide just brought about a different distribution of the food intake. The food intake was delayed in time after an injection of peptide. It was important that the rat will serve as its own control due to individual variations in the pattern of food intake.

When the experiment was completed (different dosages of peptide+ controls) the animals were killed and pancreas taken out. There was a correlation between the pattern of food intake and the amount of procolipase in the pancreatic gland. The rats which had a peptide pattern in the control had more procolipase in their pancreas and therefore possibly a larger endogenous production of peptide. This is a support for a physiological function of the peptide in the regulation of appetite and thus also for a pharmacological use.

The results are shown in the following tables.

TABLE I

Food intake during a four hour period before and after injection of peptide (20 μg). The intake of food, which is the same with and without peptide, is defined as 100 per cent and the intake is calculated as cumulative intake of food in per cent. The rat served as control one day, receiving peptide the next day etc.

| Time | Intake of food (%) Control n = 8 | Intake of food (%) Peptide (20 μg) n = 8 |
| --- | --- | --- |
| 0 | 0 | 0 |
| ½ hour | 53.5 ± 9.2 | 41.6 ± 11.0 |
| 1 hour | 76.7 ± 16.3 | 55.0 ± 5.9 |
| 2 hours | 95.9 ± 6.1 | 64.3 ± 8.2 |
| 4 hours | 100 | 100 |

Table II

Weight increase of rat fed normal food (standard pellets), of rat given standard pellets and injection of peptide (20 μg) once a week and of rat given standard pellets to which were added procolipase according to the following description: pellets weighing 2,5 g were drilled to produce a 0.5×10 mm gap, in which 50 μl of a procolipase solution (54600 units/ml) corresponding to 100 μg procolipase containing 5 μg peptide was added. With a daily consumption of 10–15 g pellets, the amount of peptide consumed corresponded to 20–30 μg peptide.

TABLE II

Weight increase of rat fed normal food (standard pellets), of rat given standard pellets and injection of peptide (20 µg) once a week and of rat given standard pellets to which were added procolipase according to the following description: pellets weighing 2,5 g were drilled or produce a 0.5 × 10 mm gap, in which 50 µl of a procolipase solution (54600 units/ml) corresponding to 100 µg procolipase containing 5 µg peptide was added. With a daily consumption of 10–15 g pellets, the amount of peptide consumed corresponded to 20–30 µg peptide.

|  | Weight increase g/day |
| --- | --- |
| Normal | 1.67 |
| Peptide (once a week) | 1.50 |
| Procolipase pellets | 0.18 |

Effect of procolipase pellets

In continued investigations it has been demonstrated that the food intake of rats can be reduced by a continous administration of procolipase pellets and that the effect is reversible, that is the food intake will go up again when the procolipase pellets are replaced by ordinary pellets. The experiments were designed in a way that 2 rats were given ordinary pellets for 10 days (period I), then procolipase pellets (3.77 nmol/g) for 10 days (period II) and finally ordinary pellets for 7 days (period III). The food was available 17 hours per day between 4.00 p.m. and 9.00 a.m. The results disclosed in table III show that the intake of food was significantly lower during the procolipase period.

TABLE III

| Experimental situation | Intake of food (g/day) |
| --- | --- |
| Period I: Standard pellets | 17.8 ± 2.6 |
| Period II: Standard pellets + procolipase | 15.0 ± 1.8*** |
| Period III: Standard pellets | 17.5 ± 2.1 n.s. |

Pellets containing the same amount of colipase (3.77 nmol/g) did not influence the intake of food, which supports the significance of the propeptide.

Procolipase in genetically obese Zucker rats

Genetically obese Zucker rats (fa/fa) have a greater bodyweight and a larger intake of food than normal laboratory rats. We have found that pancreas of the obese rats contains a significantly lower amount of procolipase than pancreas of rats of normal weight (Table IV). This supports the hypothesis that procolipase in some form is of significance for the normal control of the intake of food and in the bodyweight. Other pancreatic enzymes, lipase and trypsin, are normal.

TABLE IV

Body weight, food intake and composition of pancreas in genetically obese Zucker rats and normal rats.

|  | Normal (n = 13) | Obese (n = 4) |
| --- | --- | --- |
| Body weight (3 months) | 200.6 g | 308 g |
| Food intake (g/day) | 16.8 ± 1.1 | 21.4 ± 0.9 |
| The enzymes of pancreas: | | |
| Activity/mg protein | | |
| Amylase | 1.76 ± 0.45 | 0.78 ± 0.12** |
| Trypsinogen | 6.27 ± 1.28 | 6.07 ± 0.97 n.s |
| Lipase | 192.6 ± 36.6 | 169.0 ± 46.5 n.s |
| Procolipase | 206.1 ± 46.4 | 79.3 ± 22.9*** |

Pharmaceutical compositions

The peptide according to the invention can be administered in ordinary pharmaceutical compositions. Below is presented some proposals for compositions wherein the peptide is a constituent.

| | | |
| --- | --- | --- |
| Tablet | peptide | 5 mg |
| | lactose | 140 mg |
| | Mg-stearate | 2 mg |
| | cellulose acetate phtalate | 10 mg |
| Microcapsules | peptide | 5 mg |
| | lactose | 100 mg |
| | Avicel | 50 mg |
| | Eudragit L | 30 mg |
| iv solution | peptide | 5 mg |
| | NaOH | q.s. to alkaline pH |
| | NaCl | to isotonic |
| | pure H$_2$O | ad 1 ml |
| Nose spray | peptide | 5 mg |
| | NaOH | q.s. |
| | NaCl | q.s. |
| | Methyl cellulose | q.s. |
| | pure H$_2$O | ad 0.2 ml |
| Nose powder | peptide | 5 mg |
| | lactose | 20 mg |
| Sublinguett | peptide | 5 mg |
| | lactose | 140 mg |
| | gum arabic | 10 mg |
| | Mg-stearate | 2 mg |

I claim:

1. A method of decreasing appetite in mammals comprising administering to a mammal in need of such treatment a pharmaceutical composition comprising as active ingredient an amount of a peptide selected from the group consisting of Ala-Pro-Gly-Pro-Arg, Val-Pro-Asp-Pro-Arg, Ala-Pro-Gly-Pro-Arg having a C-terminal amide and Val-Pro-Asp-Pro-Arg having a C-terminal amide, effective to decrease the mammal's appetite.

2. A method of decreasing appetite in mammals comprising administering to a mammal in need of such treatment a pharmaceutical composition comprising as active ingredient an amount of a peptide selected from the group consisting of Ala-Pro-Gly-Pro-Arg bound to a synthetic polymer and Val-Pro-Asp-Pro-Arg bound to a synthetic polymer, effective to decrease the mammal's appetite.

3. A method of decreasing appetite in mammals comprising administering to a mammal in need of such treatment a pharmaceutical composition comprising as active ingredient an amount of human procolipase which includes at its N-terminal end the sequence Ala-Pro-Gly-Pro-Arg effective to decrease the mammal's appetite.

4. A method of decreasing appetite in mammals comprising administering to a mammal in need of such treatment a pharmaceutical composition comprising as active ingredient an amount of nonhuman procolipase which includes at its N-terminal end Val-Pro-Asp-Pro-Arg effective to decrease the mammal's appetite.

* * * * *